United States Patent [19]
Song et al.

[11] Patent Number: 5,575,773
[45] Date of Patent: Nov. 19, 1996

[54] REVERSIBLE VEIN RESIN NEEDLE SET FOR ONE TIME USE

[76] Inventors: Kyung J. Song; Young S. Song; Jerng S. Song; Joong S. Song, all of #1-Ga 57-1, Kyungwon-Dong, Wansan County, Junju City, Junbuk-Do, Rep. of Korea

[21] Appl. No.: 250,495

[22] Filed: May 27, 1994

[30] Foreign Application Priority Data

May 27, 1993 [KR] Rep. of Korea ............... 1993-9246

[51] Int. Cl.⁶ .................................................. A61M 5/00
[52] U.S. Cl. .................. 604/110; 604/158; 604/163; 128/760
[58] Field of Search ........................... 604/110, 187, 604/4, 7–9, 86, 87, 88, 191, 218, 220, 221, 222, 246, 255, 80, 158, 160, 162, 163, 257; 128/760, 763, 766–768, 770

[56] References Cited

U.S. PATENT DOCUMENTS

| | | | |
|---|---|---|---|
| 4,005,710 | 2/1977 | Zeddies et al. | 604/86 |
| 4,048,996 | 9/1977 | Mittleman et al. | 604/86 |
| 4,140,108 | 2/1979 | Nugent | 128/760 |
| 4,398,544 | 8/1983 | Nugent et al. | 128/763 |
| 4,606,734 | 8/1986 | Larkin et al. | 604/84 |
| 5,032,117 | 7/1991 | Motta | 604/88 |
| 5,122,123 | 6/1992 | Vaillancourt | 604/192 |
| 5,147,314 | 9/1992 | Vaillancourt | 604/158 |
| 5,269,317 | 12/1993 | Bennett | 128/760 |

*Primary Examiner*—Randall L. Green
*Assistant Examiner*—V. Alexander

[57] ABSTRACT

A reversible vein resin needle set for one time use designed not only to make the injection faster and convenient when injecting blood or injectant, but also to protect physicians and nurses from infection of AIDS, etc. caused by the metal needle stained by patient's blood. The device prevents the patient from infection of viruses through the metal needle by protecting the metal needle either in the cylinder of the resin needle set or in the connector, when injecting blood or injectant into the vein of a patient, by connecting the injectant container and one side of the resin needle set by the injectant line linked to the injectant regulator, and by keeping the metal needle in the cylindrical film shield or in the protective cylinder to shut off the outside. The device also protects the metal needle handling personnel from infection of AIDS and other diseases by holding the needle tip either in the cylinder or in the elastic body and in the rubber cap after the use of the metal needle.

14 Claims, 15 Drawing Sheets

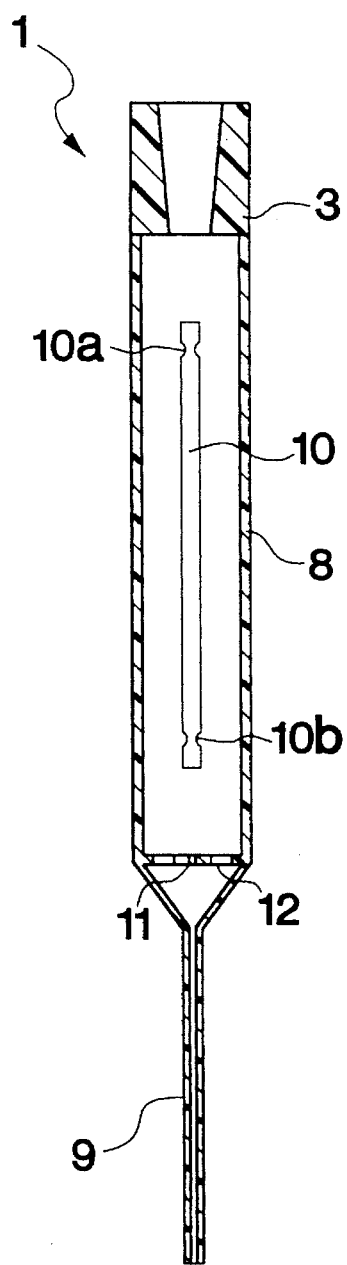
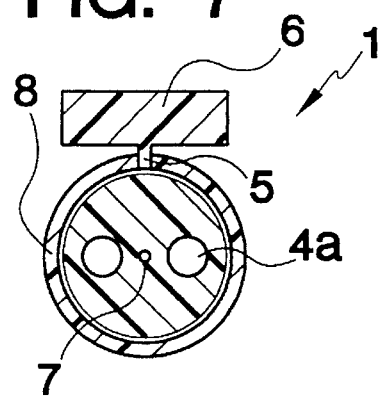
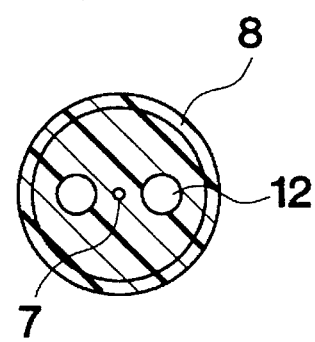
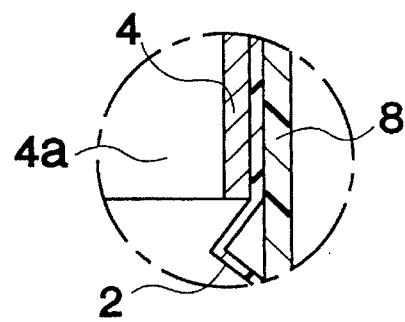

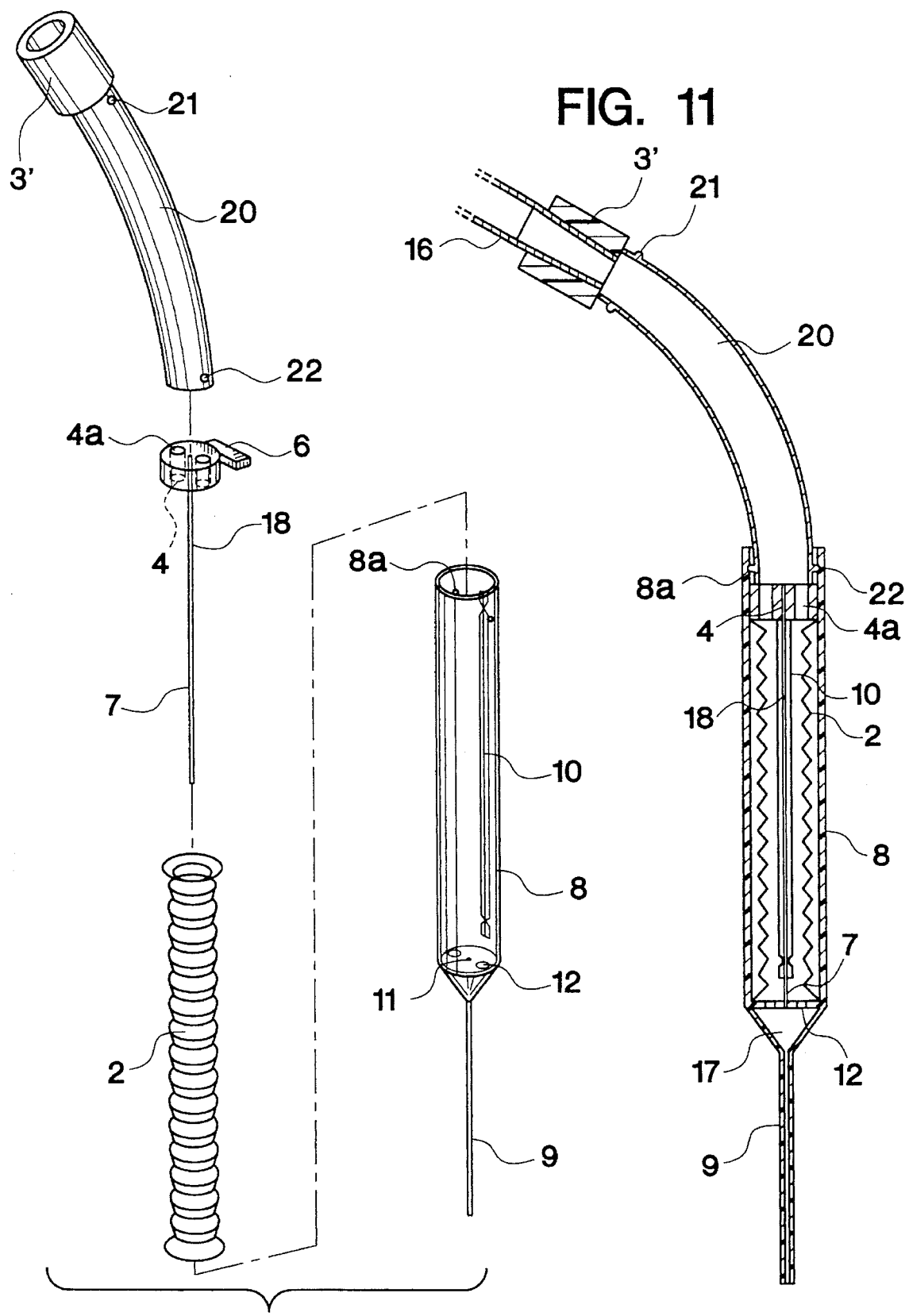

FIG. 14
FIG. 13
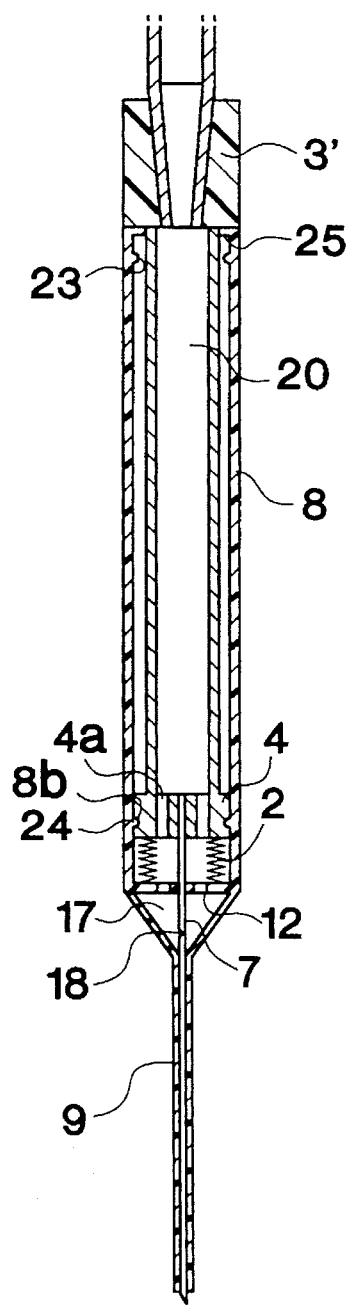
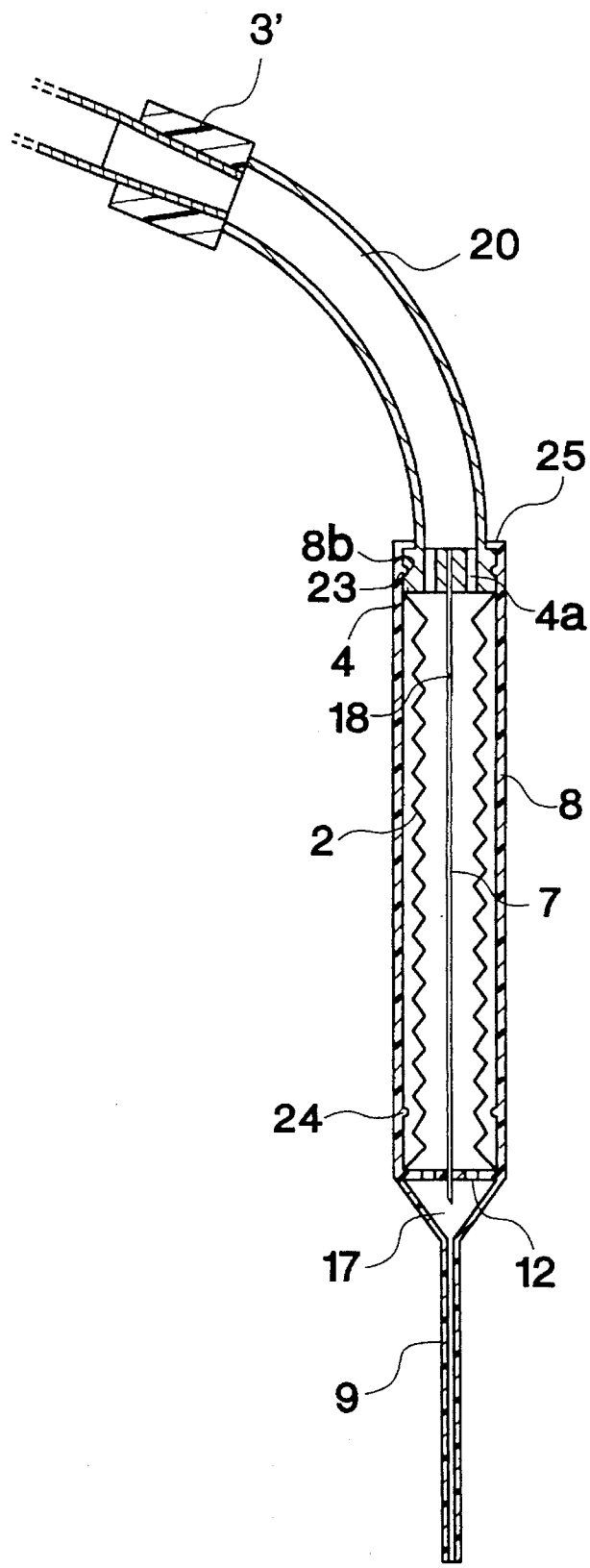

5,575,773

REVERSIBLE VEIN RESIN NEEDLE SET FOR ONE TIME USE

BACKGROUND AND SUMMARY OF THE INVENTION

This invention is related to a reversible vein resin needle for one time use that is designed to transfuse blood or injections into a vein by backing the metal needle out but not discarding it when the resin needle is being pricked into a vein.

The vein resin needle generally used these days as illustrated in FIG. 26 is pricked into a vein together with a metal needle 80 and then is connected to the connector 82 of an injectant line above the holder 82 after removing the metal needle 80.

Since the vein resin tube 81 has to be connected to the holder 82 and then to the injectant line immediately after removing the metal needle 80 from the vein, this method has the defect of leaking blood from the vein through the resin tube in the process of making the connections.

The connection process is not only inconvenient but also uneconomical since the resin tube should be replaced with a new one when the tube is to be pricked into another vein of the same patient since the metal needle 80 has been removed.

While making the connection to the injectant line, the exposed metal needle 80 may become the source of a prick wound that may infect others with a virus.

Especially, in the event of injecting the injectant into the vein of an unknown AIDS patient, when the metal needle is removed from the vein, there is a serious problem of infecting the handlers with the AIDS virus.

Therefore, the objects of the present invention are:

Firstly, to make a faster injection of blood or injectant by using a metal needle/resin tube by simply moving the metal needle backwards to clear the passage of the resin tube.

Secondly, to enable the metal needle/resin tube to prick into another vein continuously only by moving the metal needle back into the resin tube without using a new one.

Thirdly, to provide all personnel concerned, such as doctors and nurses, with infection-free reversible vein resin needles for one time use by eliminating the sources of prick wounds by the exposed metal needle.

This invention as stated above makes the vein injection easier and movable from one vein to another of the same patient repeatedly without using a new resin needle set, and has the feature that prevents the patient and the person handling the needle from being infected by a virus.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 6 shows a sectional view of the cylinder of the first embodiment;

FIG. 7 shows a sectional view of line 7—7 in FIG. 3 of the first embodiment;

FIG. 8 shows a sectional view of line 8—8 in FIG. 3 of the first embodiment;

FIG. 9 shows an enlarged view of portion A (FIG. 4) of the first embodiment;

FIG. 10 shows a view of the disassembled internal parts according to a second embodiment of the present invention;

FIG. 11 shows a sectional view of the second embodiment after the metal needle is backed out;

FIG. 13 shows a sectional view of an assembled resin needle according to a third embodiment of the present invention with the metal needle in the advanced position;

FIG. 14 shows a sectional view of the third embodiment after the metal needle is backed out;

DETAILED DESCRIPTION OF THE INVENTION

Figure 1:
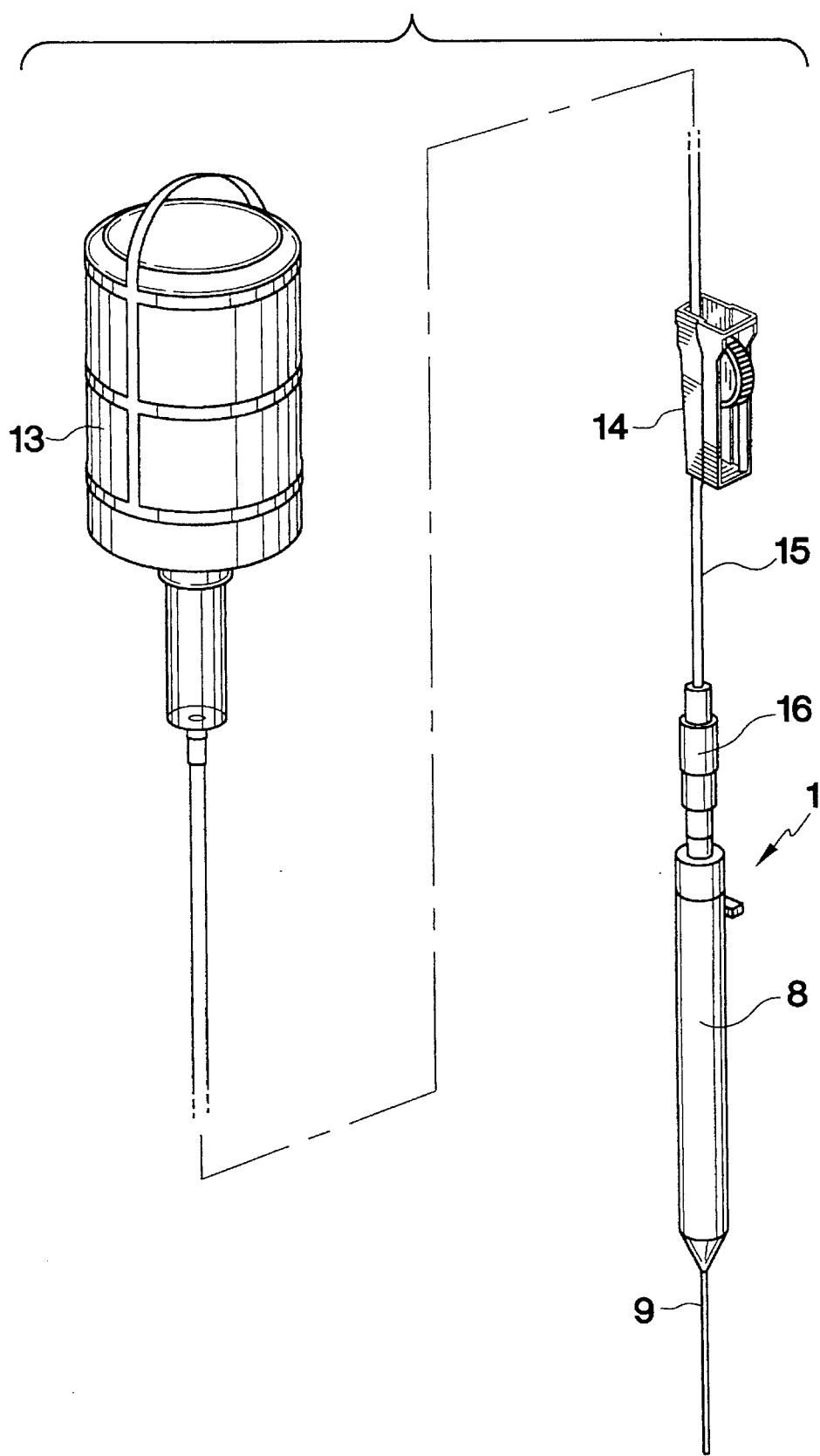
FIG. 1 shows an overall view of a reversible resin needle set according to a first embodiment of the present invention in use.
Figure 2:
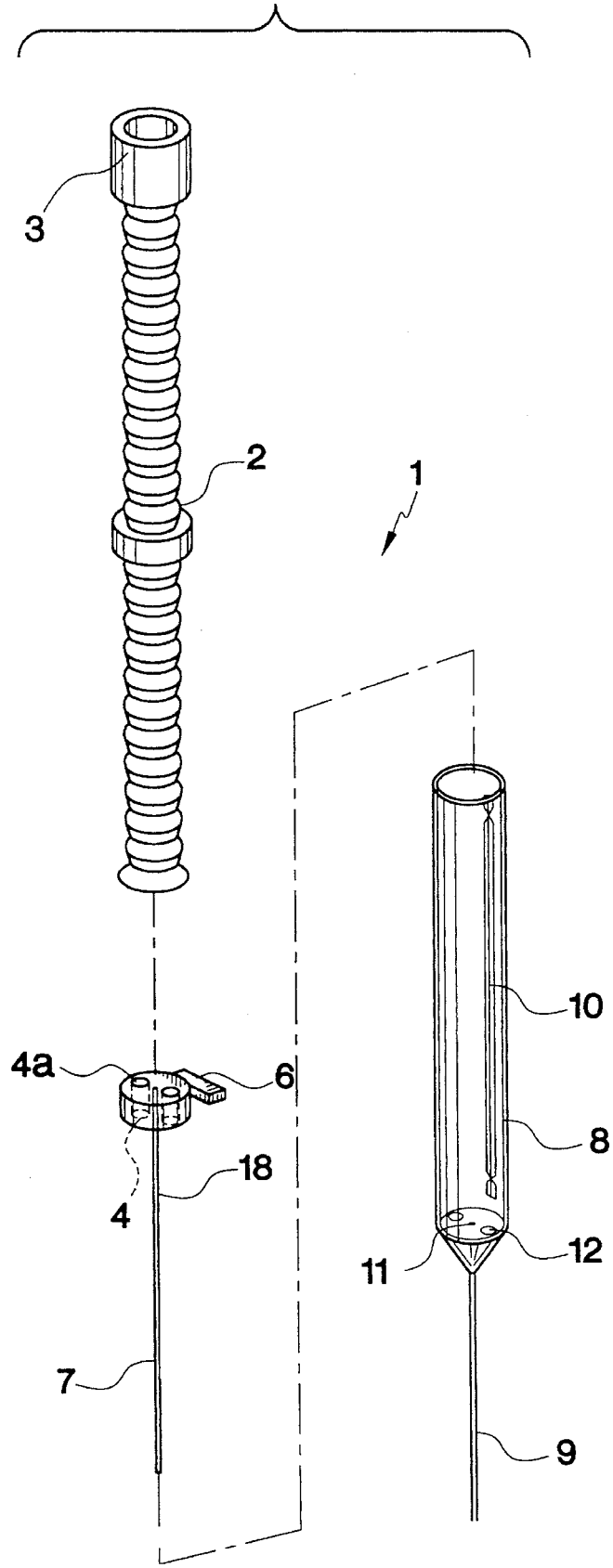
FIG. 2 shows the disassembled parts of the first embodiment.

Component parts numbered in the various figures are noted as follows:

Element 1 is a resin needle set, elements 2, 2' are cylindrical film shields, element 3 is a transfusion line connector, element 4 is a piston, element 4a is an injectant passing hole, element 5 is a connecting rod, element 6 is a knob, element 7 is a metal needle, element 8 is a cylinder, elements 8a, 8b are concave grooves, element 9 is a resin tube, element 10 is a sliding groove, elements 10a, 10b are stoppers, element 11 is a needle hole, element 12 is an injectant supply hole, element 13 is an injectant container, element 14 is an injectant regulator, element 15 is an injectant line, element 16 is a connector, element 17 is a triangular cavity, element 18 is a vent hole, element 20 is a flexible tube, elements 21, 22, 23, 24 are protrusions, element 25 is a stop, element 30 is a resin cylinder, elements 31, 33 are elastic bodies, element 32 is a connector, element 34 is a needle cylinder, element 36 is a cap, element 34 is a needle cylinder, element 36 is a cap, element 40 is a protective cylinder, element 41 is a small passage, element 42 is a female nut, element 43 is an inside cylinder, element 44 is a male nut, element 45 is a plunger, and element 46 is a rubber cap.

A detailed explanation of each embodiment of this invention follows with reference to the attached drawings.

FIGS. 1 through 9 illustrate a first embodiment of this invention.

The injectant line 15 is connected to the injectant container 13, and the injectant regulator 14 is installed at the lower part of the injectant line 15, and the connector 16 is connected to the lower end of the injectant line 15.

An upper end of the transparent cylindrical film shield 2 is closed and fixed to the transfusion line connector 3 where the connector 16 is to be inserted, and the lower end of the cylindrical shield 2 is closed and fixed from the outside of injectant supply hole 12 to the lower end of the cylinder 8, and the resin tube 9 of fixed length is installed at the lower end of the cylinder 8.

Also, the triangular cavity 17 is installed at the lower end of the cylinder 8, and the metal needle 7 includes a vent hole 18 to allow the metal needle 7 to function at the lower end of the triangular cavity 17 when the metal needle 7 reaches the point of its lower stroke.

The cylinder 8 is made of transparent or semi-transparent material.

A sliding groove 10 is located on one side of the cylinder 8 extending from its upper part to the lower part. A protrusion or a stopper 10a is formed on the upper part of the groove and another stopper 10b is formed on the lower part of the groove.

Injectant supply holes 12 are vertically formed at the connecting spot of the cylinder 8 and the resin tube 9. A needle hole 11 through which the metal needle 7 passes is formed in the center of the connecting spot.

A piston 4 is fixed on the center of the transparent cylindrical film shield and moves up and down in the cylinder 8. The piston is fixed to the metal needle 7.

Two injectant passing holes 4a are formed on both sides of the piston 4. A connecting rod 5 of the knob 6 is attached to the piston 4 through the sliding groove 10 from the outside of the cylinder 8.

The transparent cylindrical film shield 2 is fixed to the outside of the piston 4 to make the two function as one unit.

Now, the detailed explanation on the operation and the effect of the first embodiment of this invention follows.

The blood or injectant in the injectant container 13 flows by loosening the injectant regulator 14 after inserting the connector 16 extending from the injectant line 15 into the transfusion line connector 3.

Then, the blood or injectant in the injectant container 13 can be supplied to the cylindrical film shield 2 in the cylinder 8 through the injectant regulator 14 and the injectant line 15.

Figure 3:
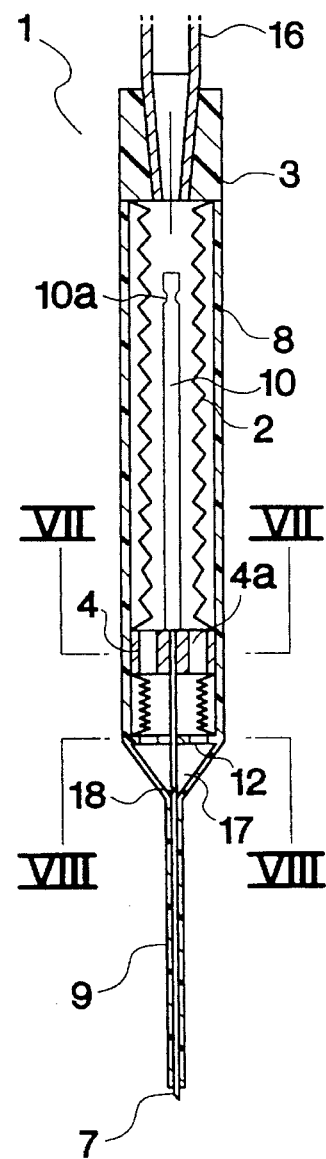
FIG. 3 shows a sectional view of an assembled resin needle with the metal needle in the advanced position of the first embodiment.

At this time, the piston 4 is located at the lower part of the cylinder 8 as shown in FIG. 3, and the metal needle 7 is protruded about 1–2 mm beyond the lower end of resin tube 9.

In use, an operator would hold the cylinder 8 together with the knob 6 and prick the metal needle 7 into the vein of the desired spot correctly. The blood in the vein then flows reversely through the metal needle 7.

The operator would then make sure that the metal needle 7 is pricked correctly in the vein by seeing reverse flow of blood.

Figure 4:
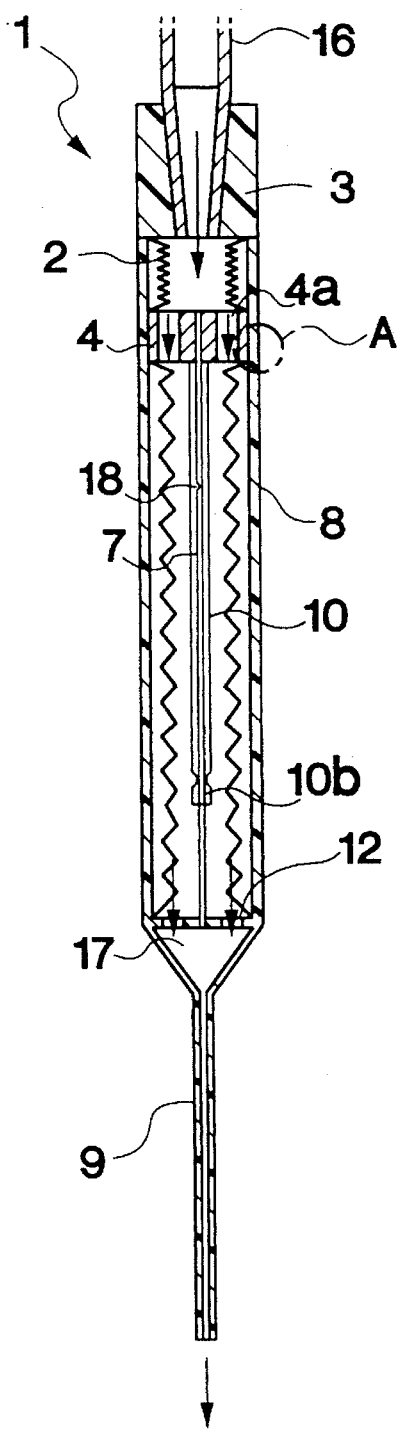
FIG. 4 shows a sectional view of the flow of injectant supply when the metal needle is in the backward position of the first embodiment.
Figure 5:
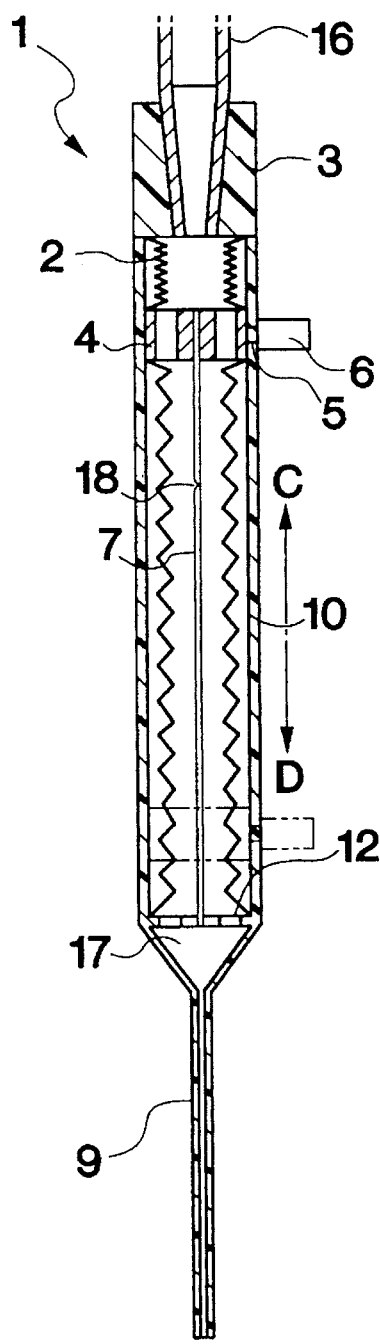
FIG. 5 shows a sectional view of the vein resin needle of the first embodiment in operation.

The operator would then hold the knob 6 and move it in the direction of C as illustrated in FIGS. 4 and 5, whereby the connecting rod 5 pushes the piston 4 upward led by the sliding groove 10.

When the metal needle 7 is located in the resin tube, the injectant supply is made through the metal needle 7 only since the resin tube 9 is blocked by the metal needle 7.

The connecting rod 5 moving upward comes to a stop at the stopper 10a of the sliding groove 10, and it is the upper stroke point of the piston 4.

At this point, the end of the metal needle 7 is located at the needle hole 11, and the injectant in the cylinder 8 is injected into the vein passing through the injectant supply holes 12 and the resin tube 9.

The triangular cavity 17 of the resin needle set 1 is supplied with blood or injectant through the injectant supply holes 12 and the cylinder 8.

The blood or the injectant supplied into the triangular cavity 17 can be transfused into the vein without letting the air in the cavity 17 flow into the vein since the air exhausts through the vent hole 18 that was finely processed by laser beam or a grinder.

Now the injectant is supplied to the cylindrical film shield 2 in the cylinder 8 through the injectant line 15, and then the blood or the injectant flows downward through the injectant passing holes 4a of the piston 4 since the cylindrical film shield 2 is fixed to upper and lower parts of the cylinder 8.

The length of the cylindrical film shield 2 is about double the length of the cylinder 8, and the cylindrical film shield 2 folds like a bellow as the piston 4 moves up and down.

In case of relocating the resin needle set 1 from one vein to another for continuous transfusion while the resin needle set 1 is used, the operator would stop the supply of blood or injectant by the injectant regulator 14, move the knob 6 in the "D" direction after the resin tube 9 is removed from the vein, then the connecting rod 5 pushes the piston 4 down to the point of its lower stroke by overcoming the stopper 10b of the sliding groove 10, and reposition the metal needle 7 to the original position.

At this time, with the metal needle 7 repositioned, the transfusion can be made at another vein of the same patient.

Therefore, when continuous injections are required for a patient, this resin needle set 1 makes the injection from one vein to another of the same patient promptly and continuously without discarding the resin needle set 1.

Since the cylindrical film shield 2 housed in the cylinder 8 is shut off from the outside, and the piston 4 is wrapped and fixed to the shield 2, it is prevented from permeation of a virus from outside even when the piston 4 moves.

The limit points of upper and lower strokes of the piston 4 are determined by stoppers 10a, 10b of the sliding groove 10, and the moving positions of the metal needle 7 are also determined by the strokes. The metal needle 7 is shut off from an outside virus by the cylindrical film shield 2. The metal needle 7 can be returned and protruded out into the resin tube 9 after removal from the tube 9.

Therefore, the resin needle set 1 makes it possible and then into inject into one vein to another immediately thereafter.

Figure 12:
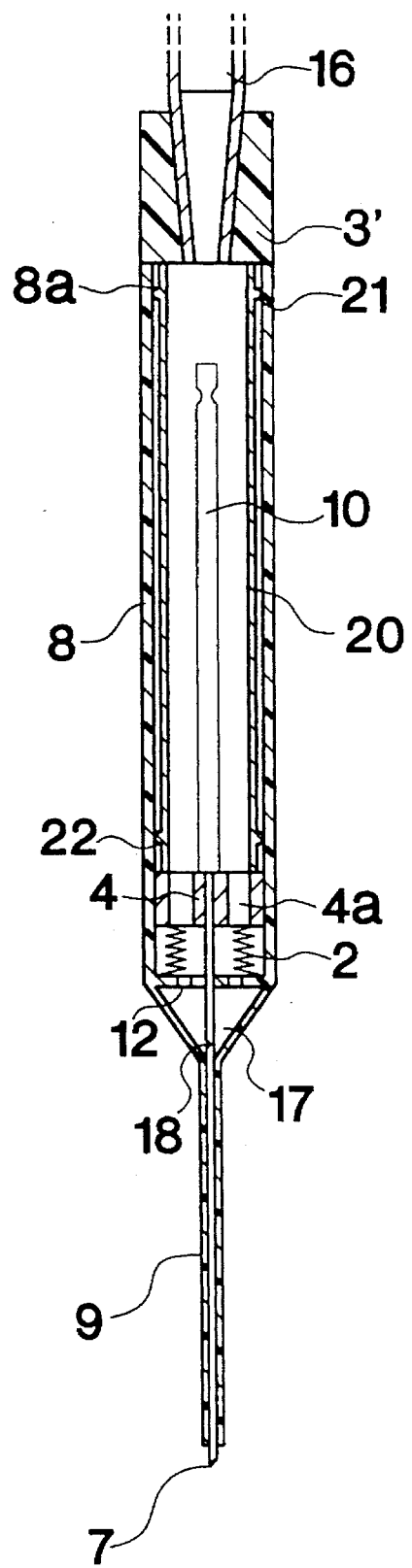
FIG. 12 shows a sectional view of an assembled resin needle of the second embodiment with the metal needle in the advanced position.
Figure 15:
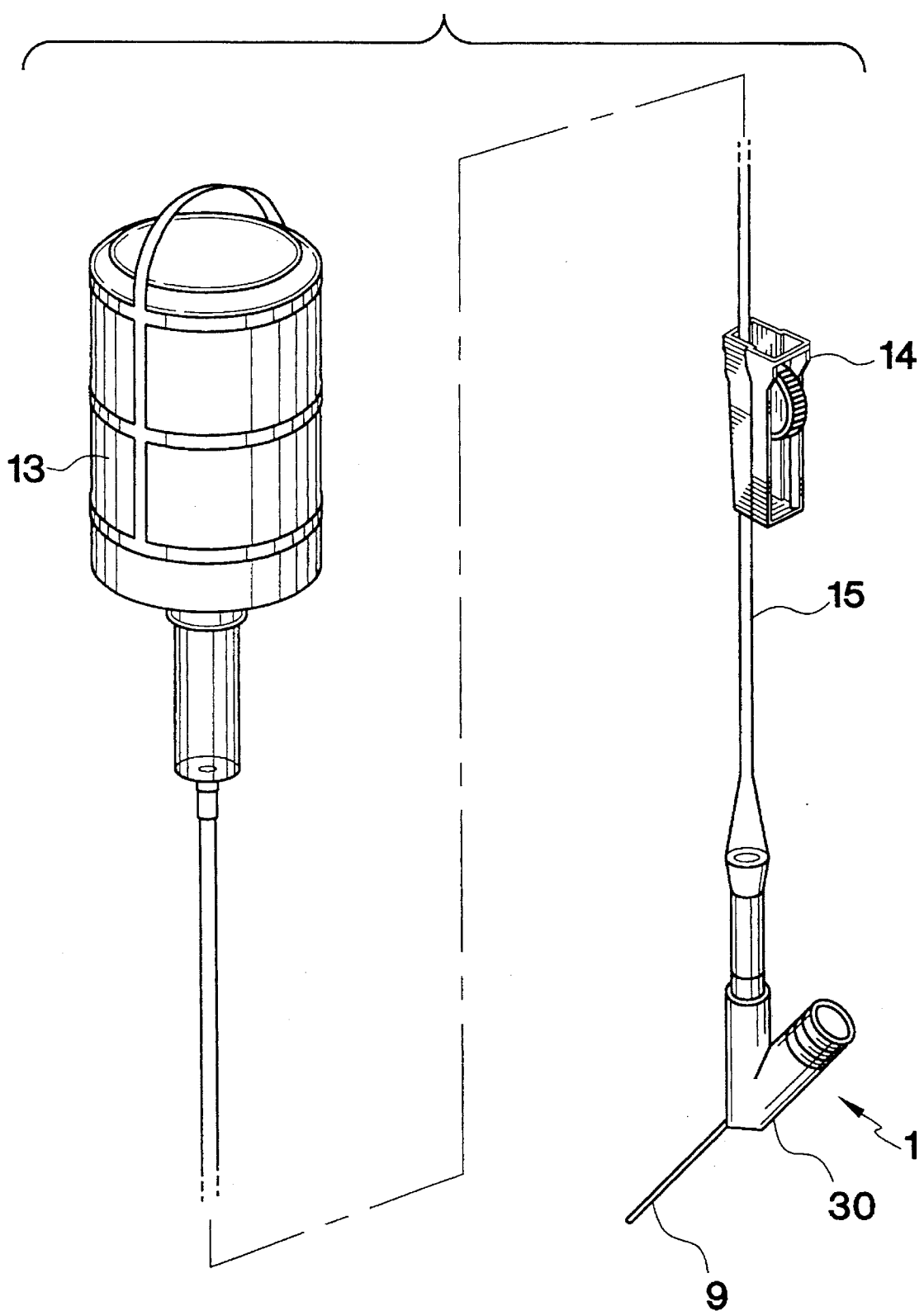
FIG. 15 shows an overall view according to a fourth embodiment of the present invention in use.
Figure 16:
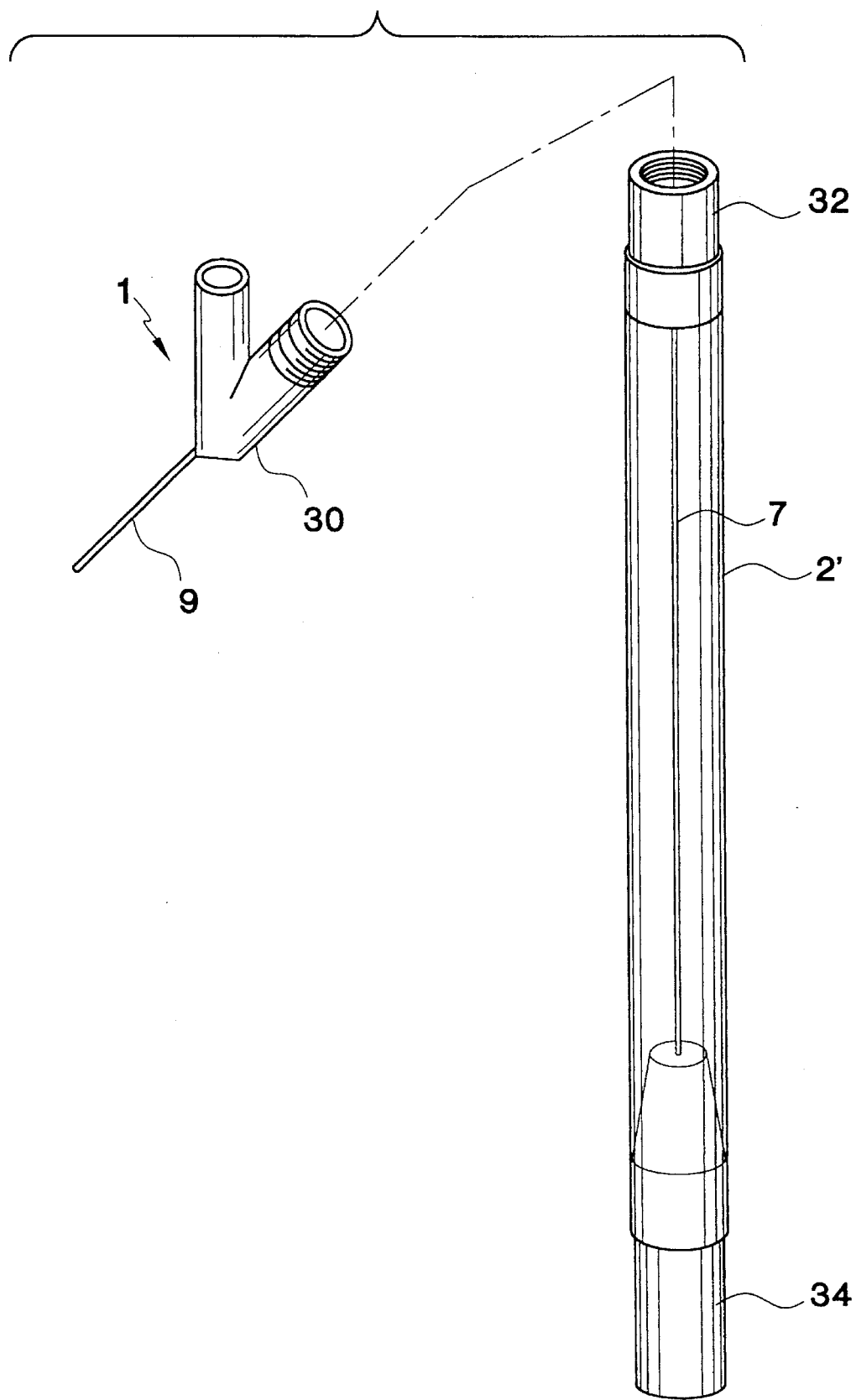
FIG. 16 shows a disassemble view of the connecting cylindrical film shield of the fourth embodiment.

FIGS. 10 through 12 illustrate a second embodiment of this invention.

Lower sides of the piston 4 having holes 4a and the cylinder 8 are connected to the upper and lower portions of the cylindrical film shield 2, and upper side of the piston 4 is connected to the flexible tube 20 of the transfusion line connector 3.

The protrusions 21, 22 are formed on upper and lower portions of the flexible tube 20, and are fitted in the concave groove 8a of the cylinder 8.

The second embodiment is used as follows:

hold the knob 6 and push the piston 4 downward, then the cylindrical film shield 2 is folded like a bellow as shown in FIG. 12, and the flexible tube 20 on the upper part of the piston 4 is inserted into the cylinder 8, and the upper protrusion 21 is fitted in the concave groove 8a formed on the upper inside of the cylinder 8 making the metal needle 7 and the resin tube 9 immediately ready for the position of pricking them into the vein.

Moving the piston 4 upwards with the knob 6 after the metal needle 7 and the resin tube 9 are pricked into the vein, then the folded cylindrical film shield 2 is stretched as illustrated in FIG. 11, and the protrusion 21 is released from the concave groove 8a and the flexible tube 20 is released from the cylinder 8, and the lower protrusion 22 of the flexible tube 20 is so fitted in the concave groove 8a of the cylinder 8 that the flexible tube 20 and the piston 4 are prevented from natural falling.

FIGS. 13 and 14 show another embodiment of this invention.

In case of moving the piston 4 back and forth during injection, hold the transfusion line connector 3' linked to the end of the flexible tube 20 and push or pull the connector 3'.

When the piston 4 is completely pulled up, the protrusion 23 formed on the upper inside of the cylinder 8 is fitted in the concave groove 8b of the piston 4, therefore, the piston 4 becomes immovable and, when the piston 4 is completely pushed down, the protrusion 24 formed at the lower inside of the cylinder 8 is fitted in the concave groove 8b of the piston 4, so the piston 4 again becomes immovable.

Element 25 is a stopping protrusion.

The flexible tube 20 should have proper hardness to not be crushed when the piston 4 is pushing down or pulling up by the transfusion line connector 3'.

FIGS. 15 through 18 illustrate a third embodiment of this invention.

One side of the resin cylinder 30 of the injectant container 13 and the resin needle set 1 is connected to the injectant line linked up to the injectant regulator 14, and the connector 32 is screwed in the other side of the resin cylinder 30 of the resin needle set 1 in which the elastic body 33 is inserted, and the needle cylinder 34 equipped with the metal needle 7 and the connector 32 are assembled to the cylindrical film shield 2, and the metal needle 7 having a vent hole 18 is protruded beyond the resin tube 9 penetrating the elastic material of the connector 32 and the same of the resin cylinder 30.

The third embodiment of this invention is composed as above.

When making an injection of blood or injectant, remove the connector 32 from the resin cylinder 30 of the resin needle set 1, and inject the injectant by adjusting its flow speed by the injectant regulator 14 linked to the injectant line 15 connecting the injectant container 13 and the resin cylinder 30.

Figure 18:
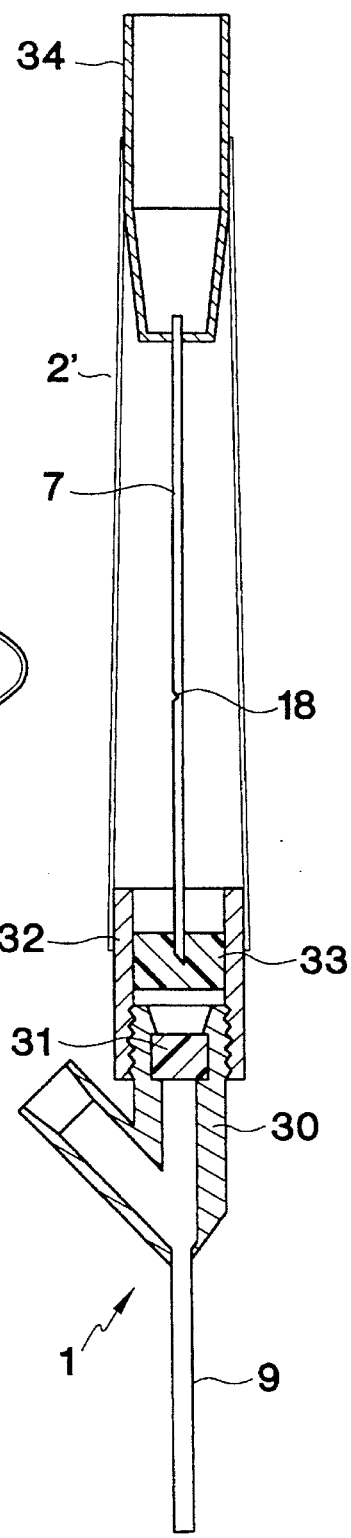
FIG. 18 shows a sectional view of the fourth embodiment after the metal needle is backed out.

That is, when making an injection of blood or injectant, inject the injectant into a vein with the metal needle 7 protruded beyond the resin tube 9 as illustrated, and locate the lower tip of the metal needle 7 to the center of the elastic material 32 in the connector 32 by pulling up the needle cylinder 34 as shown in FIG. 18 after connecting the injectant line 15 to one side of the resin cylinder 30, then the blood or injectant in the injectant container 13 is injected into the vein through the injectant line 15 and the resin cylinder 30.

And also, locate the lower tip of the metal needle 7 in the center of the elastic body 33 of the connector 32 as illustrated in FIG. 18, and remove the connector 32 that is screwed in the resin cylinder 30. Then, blood or injectant can be transfused into the vein without inflow of air and without outflow of blood or injectant since the elastic material 31 closes the space in which the metal needle 7 is pulled out by the elasticity of the elastic material.

And since the end of the metal needle 7 which is to be pulled out from the resin cylinder 30 is located in the center of the elastic body 33 in the connector 32, various virus infections can be prevented from the prick wound which may be caused by the metal needle 7 stained with the blood of a patient.

Figure 19:
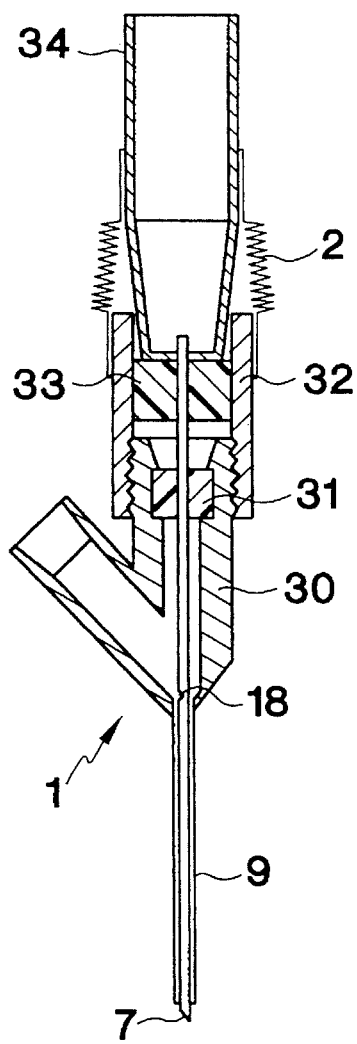
FIG. 19 shows a sectional view of an assembled resin needle according to a fifth embodiment of the present invention with the metal needle in the advanced position.
Figure 20:
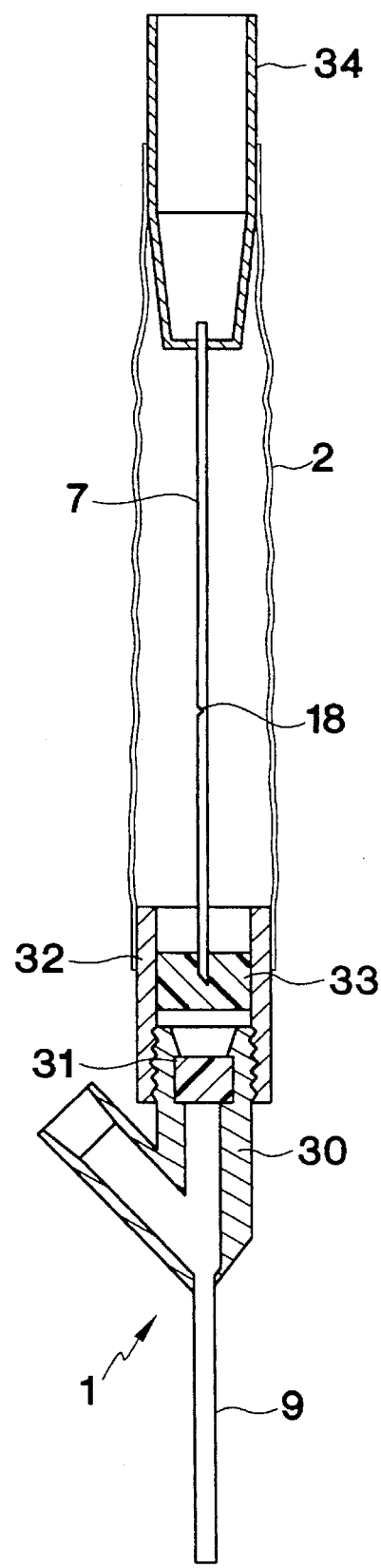
FIG. 20 shows a sectional view of the fifth embodiment after the metal needle is backed out.
Figure 21:
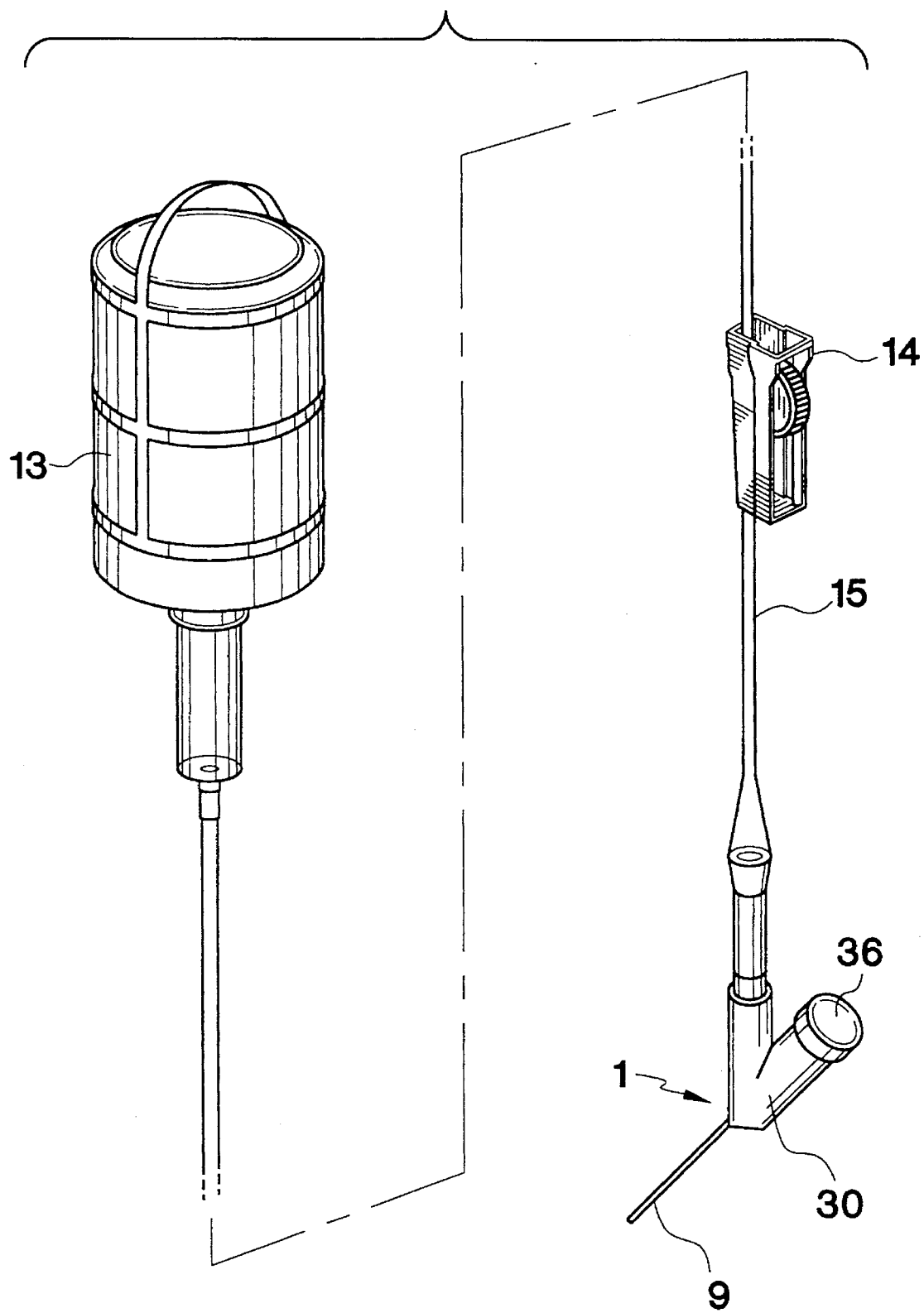
FIG. 21 shows an overall view according to a sixth embodiment of the present invention in use.
Figure 22:
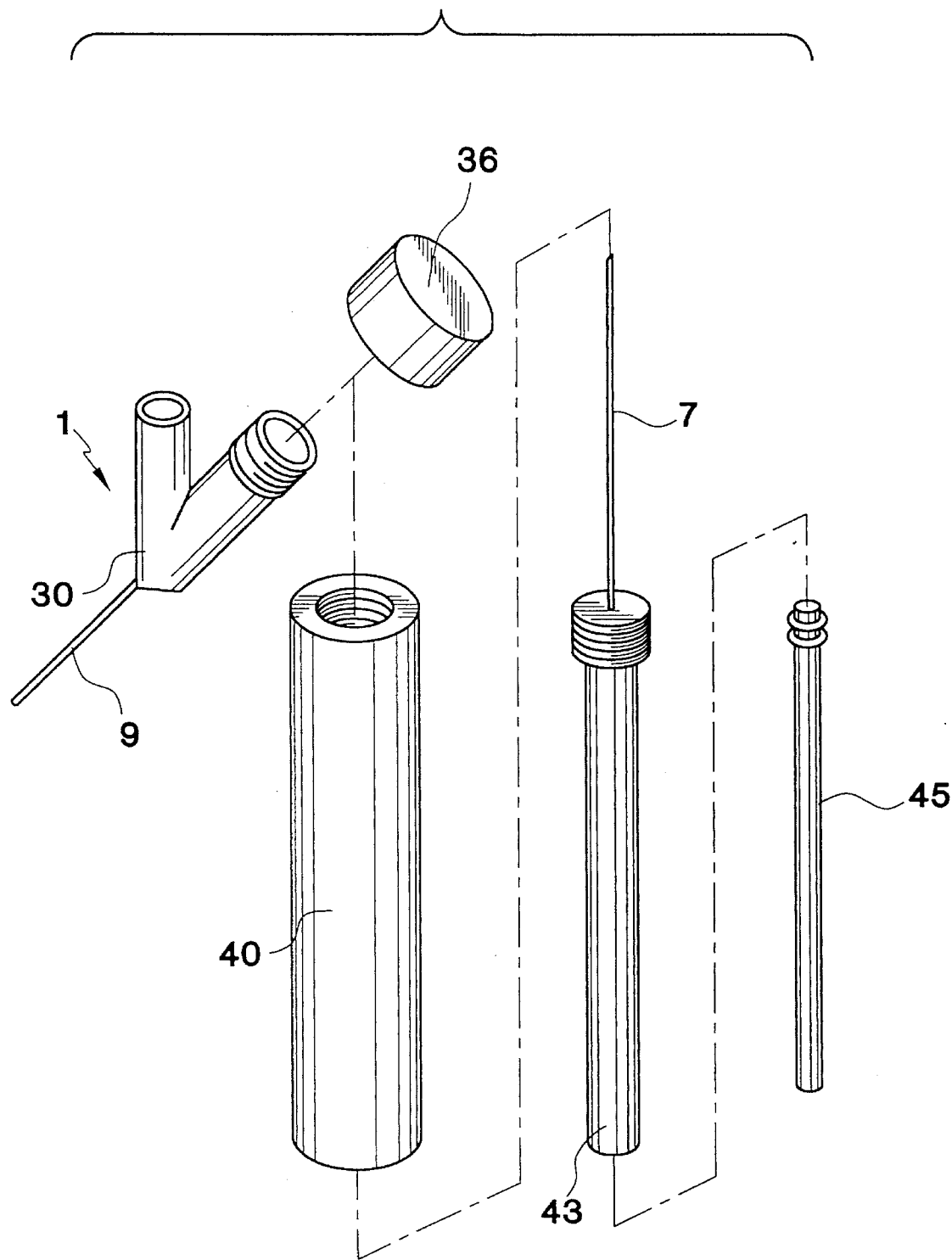
FIG. 22 shows a disassembled view of the sixth embodiment.
Figure 23:
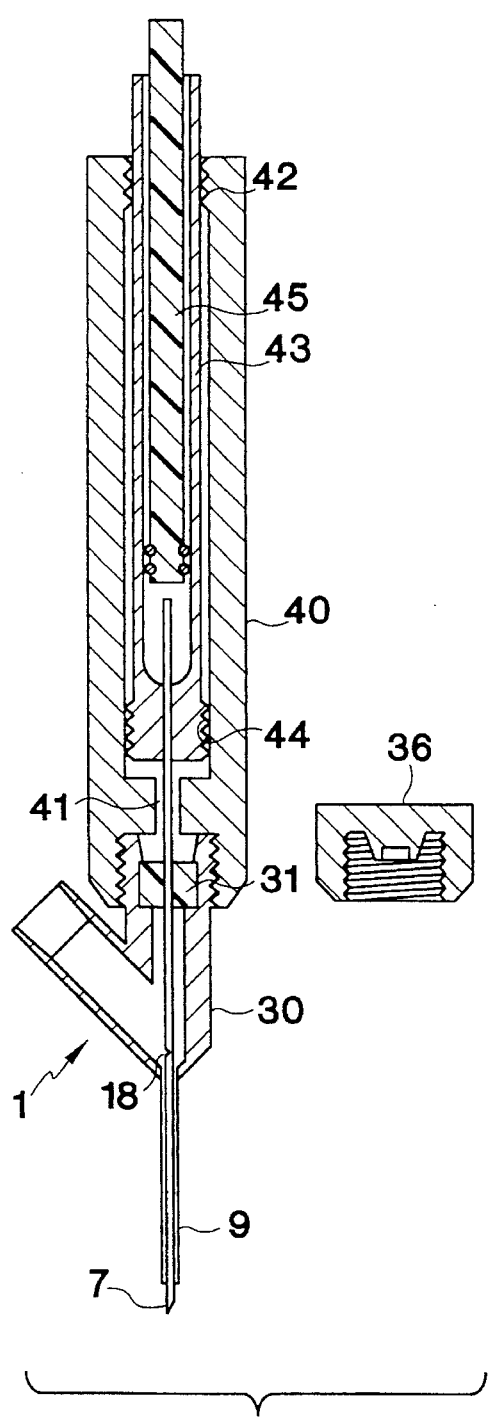
FIG. 23 shows a sectional view of an assembled resin needle according to the sixth embodiment with the metal needle in the advanced position.
Figure 24:
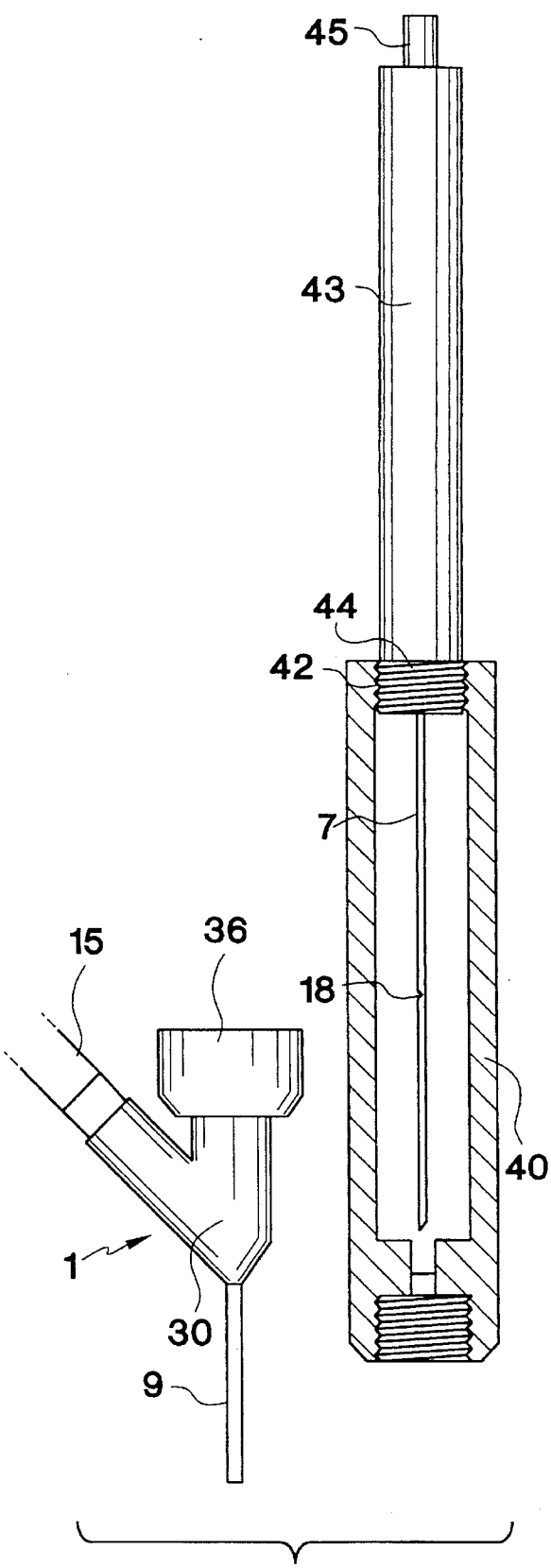
FIG. 24 shows a sectional view of the sixth embodiment after the metal needle is backed out.

FIGS. 19 and 20 illustrate a fourth embodiment of this invention.

The cylindrical film shield 2 is protected from getting damaged by means of assembling the needle cylinder 34 in which the metal needle 7 is fixed, and the connector 32 in which the resin cylinder 30 is screwed with the cylindrical film shield 2 foldable like a bellow.

Figure 17:
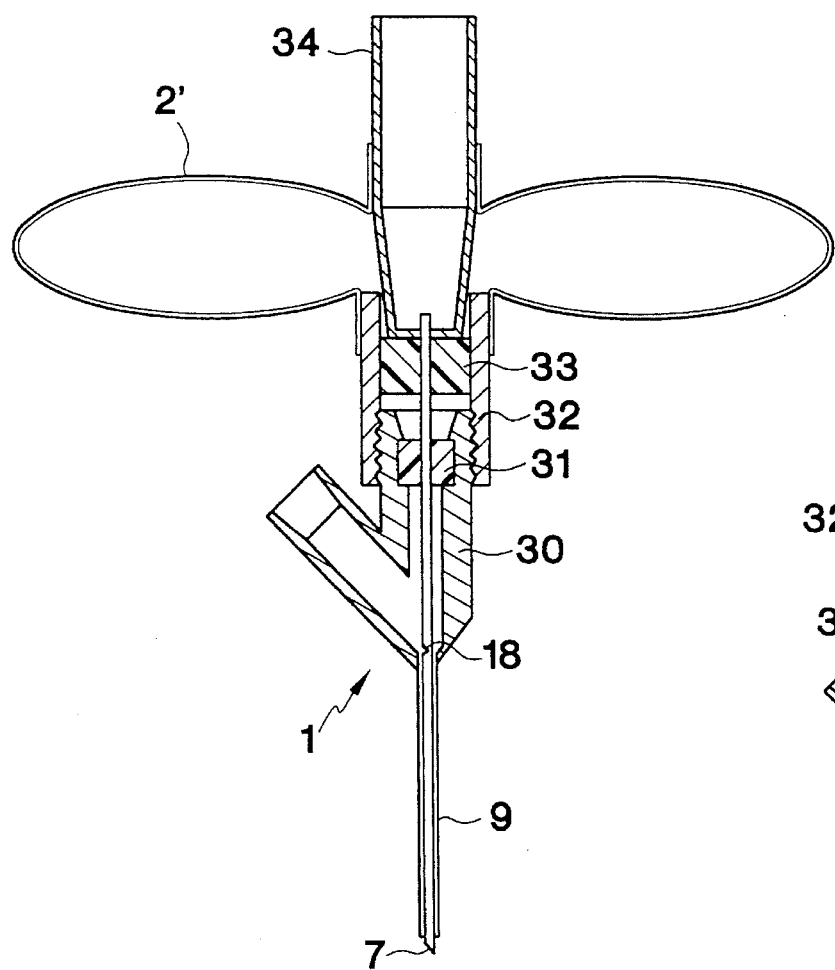
FIG. 17 shows a sectional view of an assembled resin needle of the fourth embodiment with the metal needle in the advanced position.

That is, by connecting the needle cylinder 34 and the connector 32 to the bellow-type cylindrical film shield 2, cylindrical film shield 2 can be protected from getting damaged in the position of the resin needle set 1 before its use as shown in FIG. 17.

FIGS. 21 through 24 illustrate a fifth embodiment of this invention.

Screw the protective cylinder 40 which is composed of the small passage 41 and the female nut 42 to the one side of the resin cylinder 30 connecting the injectant line 15 to the other side, and insert the inside cylinder 43 to which the metal needle 7 is attached into the protective cylinder 40, and form the male nut 44 that is screwed in the female nut 42 of the protective cylinder 40, and insert the plunger 45 into the center of the inside cylinder 43.

That is, the protective cylinder 40 is made of synthetic resin.

When the metal needle 7 is removed from the resin tube 9 by pulling up the inside cylinder 43 after the metal needle 7 and the resin tube 9 are pricked into the vein of a patient, blood or injectant can be injected.

When injecting blood or injectant, screw the cap 36 on the resin cylinder 30 after separating the protective cylinder 40 from the resin cylinder 30, therefore, permeation of virus or backward flow of blood or injectant can surely be prevented by the elastic body 31 of the resin cylinder 30.

And, when picking blood before the injection with the metal needle 7 and the resin tube 9 pricked into a vein, pull the plunger 45 inserted in the center of the inside cylinder 43, then the blood is pricked in the inside cylinder 43 through the metal needle 7 as the air in the inside cylinder 43 expands.

Figure 25:
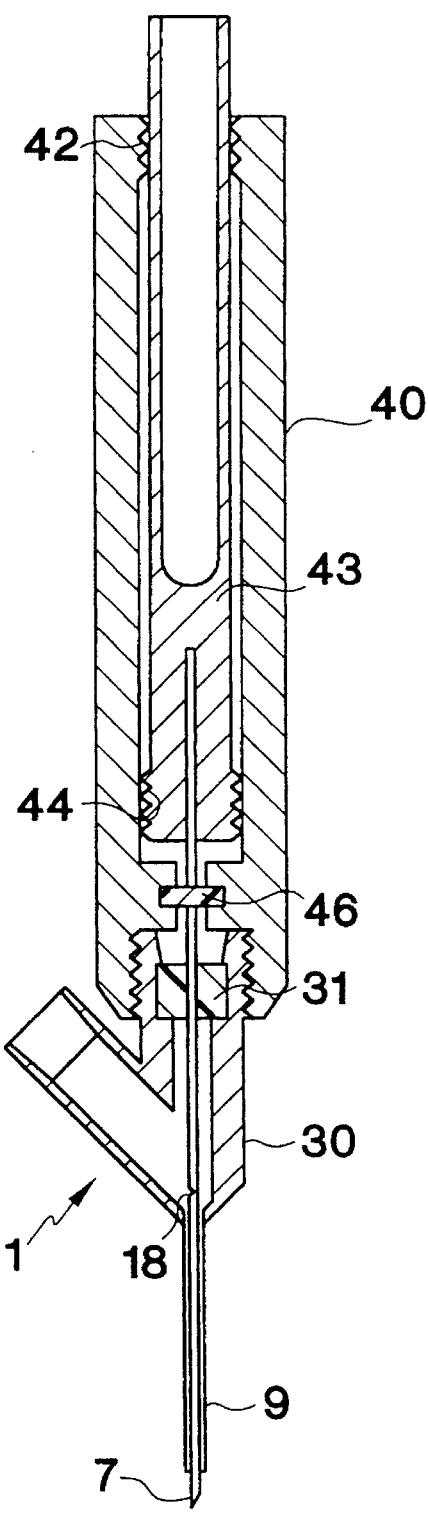
FIG. 25 shows a sectional view of an assembled resin needle according to a seventh embodiment of the present invention with the metal needle in the advanced position.
Figure 26:
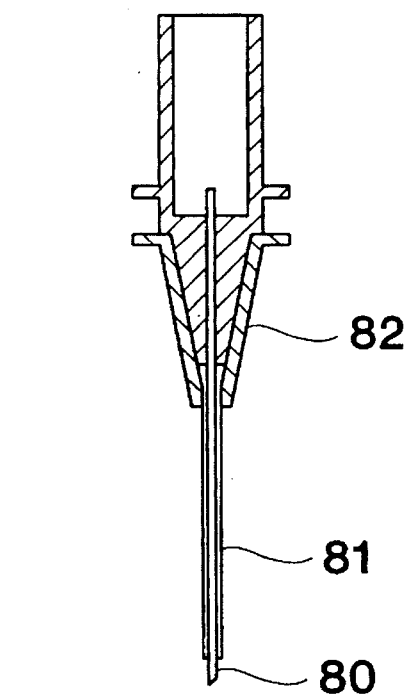
FIG. 26 shows a sectional view of a prior art resin needle.

FIG. 25 illustrates the a sixth embodiment of this invention.

By installing the rubber cap 46 at the small passage 41 of the protective cylinder 40, and when the metal needle 7 is removed from the resin tube 9 and the resin cylinder 30, a doctor or a nurse is protected from being infected with AIDS and hepatitis, etc. from a patient pricked by the metal needle 7.

This invention as stated above makes an injection of blood or injectant fast and convenient and protects backflow of blood when injecting blood or injectant into a patient's vein, connect the injectant line to one side of the resin cylinder, and pull out the metal needle after the resin tube is correctly pricked into a vein, then, this invention, as stated above, makes the injection faster and convenient and protects backflow of blood as well.

In the case of the same patient, when relocating from one vein to another during injection, injection can be made again by pushing the metal needle forward, and by pricking it into another vein and by pulling it backward with no replacement of a new metal needle, saving the time required for the replacement and preventing virus infection.

The metal needle is always protected either in the cylinder or in the connector, and is shielded from the outside by the cylindrical film shield, and is protected from permeation of a virus when using the metal needle.

Since the metal needle is discarded with its pulled back position in the cylinder, infection of AIDS or other viruses caused by pricking a wound by the metal needle can be prevented unlike a conventional needle set, and this invention is an epoch-making one.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A reversible vein needle set comprising:
    a needle body cylinder, said needle body cylinder having a transfusion line connector in which a connector of an injectant line is inserted; and
    an elongated tube having an interior portion for receipt of a metal needle therein,
    whereby said tube may be inserted into a patient, and the metal needle may be inserted into and removed from the interior portion of the tube while the tube remains in the patient,
    wherein said needle body cylinder includes an upper part and a lower part, wherein said transfusion line connector is located proximate said upper part, and wherein said reversible vein needle set further includes:
    a cylindrical film shield fixed inside of the cylinder to the upper and lower parts of the cylinder;
    a piston fixed to an interior central portion of the cylindrical film shield, said piston having a metal needle protruding downwardly therefrom;
    a knob located along a sidewall of said cylinder; and
    a connecting rod extending through said sidewall and interconnecting said piston with said knob.

2. The reversible vein needle set of claim 1, wherein the cylindrical film shield is formed as a bellows so as to be expandable and contractible along its length.

3. The reversible vein needle set of claim 2, further including:
    a sliding groove in the sidewall of the cylinder;
    a stop formed at upper and lower portions of the sliding groove;
    a needle hole formed in a central portion of the lower part of the cylinder;
    two injectant supply holes formed in the lower part of the cylinder spaced from the needle hole;
    a triangular cavity proximate said lower part of the cylinder;
    a fine vent hole formed in a sidewall of the metal needle, and
    an injectant passing hole extending through said piston.

4. The reversible vein needle set of claim 1, wherein said piston includes an injectant passing hole extending therethrough.

5. The reversible vein needle set of claim 1, further including:
    a sliding groove in the sidewall of the cylinder;
    a stop formed at upper and lower portions of the sliding groove; a needle hole formed in a central portion of the lower part of the cylinder; and
    two injectant supply holes formed in the lower part of the cylinder spaced from the needle hole.

6. The reversible vein needle set of claim 1, further including:
    a triangular cavity proximate said lower part of the cylinder, and
    a fine vent hole formed in a sidewall of the metal needle.

7. A reversible vein needle set comprising:
    a needle body cylinder, said needle body cylinder having
    a transfusion line connector in which a connector of an injectant line is inserted; and
    an elongated tube having an interior portion for receipt of a metal needle therein,
    whereby said tube may be inserted into a patient, and the metal needle may be inserted into and removed from the interior portion of the tube while the tube remains in the patient,
    wherein said needle body cylinder includes an upper part and a lower part, and wherein said reversible vein needle set further includes:
    a cylindrical film shield having a first end and a second end, said first end being connected inside of the cylinder to the lower part of the cylinder; and
    a piston movable within said cylinder, said piston being connected to said second end of said cylindrical film shield, said piston having a metal needle protruding downwardly therefrom.

8. The reversible vein needle set of claim 7, and further including:
    a flexible tube having a first end and a second end, said first end of said flexible tube being attached to said transfusion line connector, said second end of said flexible tube being attached to said piston.

9. The reversible vein needle set of claim 8, further including:

an annular groove formed in said upper part of said cylinder; and a pair of annular projections formed at spaced locations along said flexible tube for mating with said annular groove.

10. The reversible vein needle set of claim 9, further including:

a knob located along a sidewall of said cylinder;

a sliding groove formed in a sidewall of the cylinder;

a connecting rod extending through said sliding groove and interconnecting said piston with said knob;

a stop formed at upper and lower portions of the sliding groove;

a needle hole formed in a central portion of the lower part of the cylinder;

two injectant supply holes formed in the lower part of the cylinder spaced from the needle hole;

a triangular cavity proximate said lower part of the cylinder; and a fine vent hole formed in a sidewall of the metal needle.

11. The reversible vein needle set of claim 8, further including:

an annular groove formed in said piston; and an annular projection formed on each of the upper and lower parts of said cylinder for mating with said annular groove.

12. The reversible vein needle set of claim 11, further including:

a needle hole formed in a central portion of the lower part of the cylinder;

two injectant supply holes formed in the lower part of the cylinder spaced from the needle hole;

a triangular cavity proximate said lower part of the cylinder; and a fine vent hole formed in a sidewall of the metal needle.

13. A reversible vein needle set comprising:

a needle body cylinder, said needle body cylinder having a transfusion line connector in which a connector of an injectant line is inserted; and an elongated tube having an interior portion for receipt of a metal needle therein, whereby said tube may be inserted into a patient, and the metal needle may be inserted into and removed from the interior portion of the tube while the tube remains in the patient;

wherein said needle body cylinder includes a threaded portion, and wherein said reversible vein needle set further includes:

a needle assembly including a needle body, said needle body having a metal needle extending therefrom, a threaded connector for connecting with said threaded portion of said needle body cylinder, and a cylindrical film shield surrounding said metal needle and interconnecting said needle body and said threaded connector, wherein the cylindrical film shield is formed as a bellows so as to be expandable and contractible along its length.

14. A reversible vein needle set comprising:

a needle body cylinder, said needle body cylinder having a transfusion line connector in which a connector of an injectant line is inserted; and an elongated tube having an interior portion for receipt of a metal needle therein,.

whereby said tube may be inserted into a patient, and the metal needle may be inserted into and removed from the interior portion of the tube while the tube remains in the patient;

wherein said needle body cylinder includes a threaded portion, and wherein said reversible vein needle set further includes:

a needle assembly including a protective cylinder threadably engaged with said threaded portion of said needle body cylinder, an inside cylinder movable within said protective cylinder, said inside cylinder having a metal needle extending therefrom, wherein said needle assembly further includes a plunger movable within said inside cylinder.

* * * * *